(12) United States Patent
Stobrawa et al.

(10) Patent No.: US 10,179,069 B2
(45) Date of Patent: Jan. 15, 2019

(54) DEVICE AND METHOD FOR PRODUCING CONTROL DATA FOR THE SURGICAL CORRECTION OF DEFECTIVE EYE VISION (75) Inventors: Gregor Stobrawa, Jena (DE); Mark Bischoff, Jena (DE); Michael Bergt, Weimar (DE)

(73) Assignee: Carl Zeiss Meditec AG, Jena (DE)

( * ) Notice: Subject to any disclaimer, the term of this patent is extended or adjusted under 35 U.S.C. 154(b) by 1979 days.

(21) Appl. No.: 13/145,759

(22) PCT Filed: Jan. 21, 2010

(86) PCT No.: PCT/EP2010/050701
§ 371 (c)(1),
(2), (4) Date: Oct. 5, 2011

(87) PCT Pub. No.: WO2010/084163
PCT Pub. Date: Jul. 29, 2010

(65) Prior Publication Data
US 2012/0035598 A1    Feb. 9, 2012

(30) Foreign Application Priority Data

Jan. 21, 2009   (DE) .................. 10 2009 005 482

(51) Int. Cl.
*A61F 9/008*    (2006.01)
(52) U.S. Cl.
CPC .......... *A61F 9/008* (2013.01); *A61F 9/00827* (2013.01); *A61F 9/00836* (2013.01);
(Continued)

(58) Field of Classification Search
CPC ............................. A61F 9/008–9/009
(Continued)

(56) References Cited

U.S. PATENT DOCUMENTS 5,549,632 A    8/1996   Lai
5,656,186 A    8/1997   Mourou et al.
(Continued)

FOREIGN PATENT DOCUMENTS

DE    695 00 997 T2    4/1998
DE    103 34 110 A1    2/2005
(Continued)

*Primary Examiner* — Nathan J Jenness
(74) *Attorney, Agent, or Firm* — Patterson Thuente Pedersen, P.A.

(57) ABSTRACT

A device for producing control data for a laser device for the surgical correction of defective vision. The device produces the control data such that the laser emits the laser radiation such that a volume in the cornea is isolated. The device calculates a radius of curvature $R_{CV}^*$ to determine the control data, the cornea reduced by the volume having the radius of curvature $R_{CV}^*$ and the radius of curvature being site-specific and satisfying the following equation: $R_{CV}^*(r,\varphi)=1/((1/R_{CV}(r,\varphi))+B_{COR}(r,\varphi)/(n_c-1))+F$, wherein $R_{CV}(r,\varphi)$ is the local radius of curvature of the cornea before the volume is removed, $n_c$ is the refractive index of the material of the cornea, F is a coefficient, and $B_{COR}(r,\varphi)$ is the local change in refractive force required for the desired correction of defective vision in a plane lying in the vertex of the cornea, and at least two radii r1 and r2 satisfy the equation $B_{COR}(r=r1,\varphi)\neq B_{COR}(r=r2,\varphi)$.

5 Claims, 6 Drawing Sheets

(52) U.S. Cl.
CPC ....... *A61F 9/00829* (2013.01); *A61F 9/00838* (2013.01); *A61F 2009/0088* (2013.01); *A61F 2009/00872* (2013.01); *A61F 2009/00882* (2013.01)

(58) Field of Classification Search
USPC .......................................... 606/4–6; 382/128
See application file for complete search history.

(56) References Cited

U.S. PATENT DOCUMENTS

| | | | |
|---|---|---|---|
| 5,891,131 | A * | 4/1999 | Rajan et al. ...................... 606/5 |
| 5,993,438 | A | 11/1999 | Juhasz et al. |
| 6,099,522 | A * | 8/2000 | Knopp et al. ................... 606/10 |
| 6,110,166 | A | 8/2000 | Juhasz |
| 6,467,907 | B1 | 10/2002 | Fujieda et al. |
| 7,131,968 | B2 | 11/2006 | Bendett et al. |
| 2001/0010003 | A1 | 7/2001 | Lai |
| 2004/0054358 | A1 * | 3/2004 | Cox et al. .......................... 606/5 |
| 2004/0070761 | A1 | 4/2004 | Horvath et al. |
| 2004/0169820 | A1 | 9/2004 | Dai et al. |
| 2005/0107775 | A1 | 5/2005 | Huang et al. |
| 2007/0173793 | A1 * | 7/2007 | Rathjen ............................. 606/4 |
| 2007/0179483 | A1 | 8/2007 | Muhlhoff et al. |
| 2007/0293851 | A1 | 12/2007 | Muhlhoff et al. |
| 2008/0021443 | A1 | 1/2008 | Bischoff et al. |
| 2008/0082088 | A1 * | 4/2008 | Kurtz et al. ...................... 606/5 |
| 2008/0195086 | A1 | 8/2008 | Schroeder et al. |
| 2008/0234707 | A1 | 9/2008 | Muehlhoff et al. |
| 2008/0252848 | A1 | 10/2008 | Dai |
| 2008/0319428 | A1 | 12/2008 | Wiechmann et al. |
| 2009/0171327 | A1 * | 7/2009 | Kurtz et al. ...................... 606/6 |
| 2010/0256965 | A1 * | 10/2010 | Rathjen .......................... 703/11 |
| 2010/0331830 | A1 | 12/2010 | Bischoff et al. |
| 2010/0331831 | A1 | 12/2010 | Bischoff et al. |
| 2011/0034911 | A1 | 2/2011 | Bischoff et al. |

FOREIGN PATENT DOCUMENTS

| | | |
|---|---|---|
| DE | 103 58 927 A1 | 7/2005 |
| DE | 10 2005 013 558 A1 | 9/2006 |
| DE | 10 2006 053 118 A1 | 5/2008 |
| DE | 10 2006 053 119 A1 | 5/2008 |
| DE | 10 2006 053 120 A1 | 5/2008 |
| DE | 10 2007 053 281 A1 | 5/2009 |
| DE | 10 2007 053 283 A1 | 5/2009 |
| DE | 10 2008 017 293 A1 | 10/2009 |
| EP | 1 153 584 A1 | 11/2001 |
| EP | 1 159 986 A2 | 12/2001 |
| WO | WO 96/11655 | 4/1996 |
| WO | WO 2004/032810 A2 | 4/2004 |
| WO | WO 2005/011546 A1 | 2/2005 |
| WO | WO 2005/011547 A1 | 2/2005 |
| WO | WO 2005/092172 A1 | 10/2005 |
| WO | WO 2007/022993 A2 | 3/2007 |
| WO | WO 2008/055697 A1 | 5/2008 |
| WO | WO 2008/055705 A1 | 5/2008 |
| WO | WO 2009/124668 A2 | 10/2009 |

* cited by examiner

DEVICE AND METHOD FOR PRODUCING CONTROL DATA FOR THE SURGICAL CORRECTION OF DEFECTIVE EYE VISION

PRIORITY CLAIM

The present application is a National Phase entry of PCT Application No. PCT/EP2010/050701, filed Jan. 21, 2010, which claims priority from German Application Number 102009005482.0, filed Jan. 21, 2009, the disclosures of which are hereby incorporated by reference herein in their entirety.

FIELD OF THE INVENTION

In a first variant the invention relates to a device for generating control data for controlling a laser for the surgical correction of the defective vision of an eye of a patient, wherein the control data are adapted to control a laser which cuts cornea tissue by irradiating laser radiation into the cornea of the eye, the device generates the control data such that the laser, during operation according to the control data, emits the laser radiation such that a volume in the cornea is isolated, the removal of which from the cornea effects the desired correction of defective vision and, to determine the control data, the device calculates a radius of curvature that the cornea has when reduced by the volume.

In the first variant the invention further relates to a method for generating control data for controlling a laser for the surgical correction of the defective vision of an eye of a patient, wherein the control data are adapted to control a laser which cuts cornea tissue by irradiating laser radiation into the cornea of the eye, the control data are generated such that the laser, during operation according to the control data, emits the laser radiation such that a volume in the cornea is isolated, the removal of which from the cornea effects the desired correction of defective vision and, to determine the control data, a radius of curvature that the cornea has when reduced by the volume is calculated.

In a second variant the invention relates to a method for generating control data which are adapted to control a laser for the surgical correction of the defective vision of an eye of a patient, wherein, during operation of the laser, the cornea is deformed by pressing its anterior surface against a contact surface, wherein in the method a correction surface is predetermined for the non-deformed cornea, which correction surface is to be generated for correction of defective vision as a cut surface in the cornea, and wherein, in the method, the deformation of the cornea during operation of the laser is taken into account by a transformation of the coordinates for points in the non-deformed cornea into coordinates of the same points in the deformed cornea.

In the second variant the invention further relates to a device for generating control data which are adapted to control a laser for the surgical correction of the defective vision of an eye of a patient, wherein, during operation of the laser, the cornea is deformed by pressing its anterior surface against a contact surface and wherein a correction surface is predetermined for the non-deformed cornea, which correction surface is to be generated for correction of defective vision as a cut surface in the cornea, and wherein the device, during generating of the control data, takes into account the deformation of the cornea during operation of the laser by a transformation of the coordinates for points in the non-deformed cornea into coordinates of the same points in the deformed cornea.

BACKGROUND

Spectacles are the traditional way of correcting defective vision in the human eye. However, refractive surgery which corrects defective vision by altering the cornea is now also increasingly being used. The aim of the surgical methods is to selectively alter the cornea so as to influence refraction. Differing procedures of surgeries are known for this purpose. Currently the most widespread is the so-called laser-assisted in situ keratomileusis, also abbreviated to LASIK. Firstly, a lamella of the cornea is cut on one side from the cornea surface and folded to the side. This lamella can be cut by means of a mechanical microkeratome or also by means of a so-called laser keratome, such as is marketed e.g. by Intralase Corp., Irvine, USA. After the lamella has been cut and folded to the side, the LASIK operation uses an excimer laser, which removes the thus-exposed corneal tissue by ablation. After volume in the cornea has been vaporized in this manner the lamella of the cornea is folded back into its original place.

The use of a laser keratome to expose the lamella is advantageous as the danger of infection is thereby reduced and the cut quality increased. In particular the lamella can be produced with a very much more consistent thickness. The cut is also potentially smoother, which reduces sight problems due to this boundary surface which remains even after the operation.

To produce the cut, a series of incisions of the eye are made at predetermined points such that the cut surface is formed as a result. With the laser keratome the cut surface forms the lamella to be folded back before the use of laser ablation.

With the conventional LASIK method exposed corneal tissue is vaporized, which is also called "grinding" of the cornea by means of laser radiation. The volume removal which is necessary to correct defective vision is set for each surface element of the exposed cornea by the number of laser pulses and their energy. Therefore, in the LASIK method, a so-called shot file is provided for the ablation laser which defines, for different points on the cornea, how often, and with what energy, the laser beam is to be directed onto defined points on the cornea. The volume removal is heuristically determined, not least because it depends greatly on the ablation effect of the laser beam, therefore on the wavelength, fluence etc. of the radiation used. The state of the cornea also plays a role; in particular the moisture content of the cornea is to be mentioned here. WO 96/11655 describes a device and a process for the LASIK method. In particular a formula is given which calculates the radius of curvature to be achieved from the pre-operative radius of curvature of the cornea and the desired diopter correction. A similar calculation is described in EP 1153584 A1—also for corneal ablation by means of LASIK.

U.S. Pat. No. 5,993,438 proposes the removal of a volume from the cornea by vaporization and absorption in the cornea.

WO 2005/092172 discloses how optical refraction power measurements which have been determined in one plane can be transferred into another plane. The document mentions that this process can be used for different eye treatments, in particular for laser-supported ablation.

A further laser-based eye surgery method is not to vaporize the volume to be removed from the cornea, but to isolate it by a laser cut. The volume is thus no longer ablated, but isolated in the cornea by a three-dimensional cut surface and thus made removable. Empirical values which have been developed for grinding the cornea by means of ablation laser radiation cannot be used for such methods. Instead, control data are required to operate the laser for isolating the volume to be removed from the cornea. One such procedure for eye surgery is described in U.S. Pat. No. 6,110,166 and U.S. Pat. No. 7,131,968. Different volume forms are shown in U.S. Pat. No. 6,110,166 and it is mentioned that the proper volume can be chosen by a person skilled in the art.

DE 102006053118 A1 describes the production of control data for the volume-isolating correction of defective vision.

It is known from DE 102006053120 A1 and DE 102006053119 A1 from Carl Zeiss Meditec AG to base the production of such defective vision on data which give the optical refraction power of spectacles suitable for correcting defective vision. It is also known from this published document, which thus describes a method of the mentioned type and a device of the mentioned type, to use data which also bring about a correction of an astigmatism or corrections of higher-order aberrations. By using data for defective vision which are intended for a conventional spectacle correction, the approach known from DE 102006053120 A1 achieves a considerable simplification in pre-operative eye measurement, as the production of spectacle correction data is daily practice in ophthalmology. However, this simplification also means a degree of limitation of the possible correction results, because inevitably only corrections which would also be possible with normal spectacles can be achieved. It is also to be taken into account here that corrections such as are possible e.g. with varifocals are ruled out for the approach according to DE 102006053120 A1 as such corrections always assume that, depending on the viewing direction, the axis of vision passes through the spectacle lens at different points, which makes it possible to be able to bring different optical properties of the spectacles to bear for different viewing directions (e.g. reading directed more downwards, or viewing directed more into the distance). This does not apply in the case of refractive surgery on the cornea because movement of the eye obviously causes the cornea to move as well when the direction of viewing changes. Thus, unlike with a spectacle lens, there is no change in the point where the optical axis penetrates the cornea when the eyeball rotates. The approach known from DE 102006053120 A1 can thus consequently use only comparatively simple spectacle defective-vision correction data as an input variable for control data, with the consequence of correspondingly limited possibilities of correction.

The precision with which the necessary cut surfaces are produced is of great importance for volume-isolating correction of defective vision. Unlike with a laser keratome, the position of the cut surfaces has a direct effect on the quality of the optical correction. With the conventional LASIK method, on the other hand, the precision with which the laser ablation is carried out is the only important factor determining the quality of the optical correction. This can already be seen from the fact that the cornea lamella is or has been produced in a large number of operations with a relatively crudely operating mechanical knife.

As the exact positioning of the eye is important for the precision production of the cut surfaces, the state of the art, for example WO 2005/011547 A1, proposes that a contact glass, against which the cornea is pressed, can be used in laser-surgery devices. This contact glass serves to fix the eye.

However, the precise position of the eye is not the only important factor for the precision of the cut surfaces; the shape of the cornea must also be known. As this varies from patient to patient within specific ranges, the contact glass also serves to give the cornea front surface a fixed, defined shape. When pressing the front of the cornea against the contact glass, there is consequently a deformation of the cornea which varies in size, depending on the deviation of the curvature of the contact glass from the natural curvature of the cornea of the respective patient.

If the position of the cut surfaces is important for the optical correction, i.e. if not just a lamella is isolated and the volume to be removed is removed by ablation, the deformation of the cornea is essential when determining the target coordinates for producing the cut surfaces. Therefore it is known in the state of the art to take into account the deformation by subjecting the previously determined target points to a coordinate transformation. In the named WO publication, this transformation is called a "contact pressure transformation" and there are transformation equations for a combination of spherical contact glass and spherical cornea front surface. DE 102008017293 A1 from Carl Zeiss Meditec AG complements these transformation equations with the result that coordinate transformation can also be carried out on different types of contact glasses and cornea curvatures.

The invention thus relates to the concept of carrying out a correction of the optical imaging errors of the human eye by cutting, by means of laser radiation within the cornea, a volume of tissue which is then removed from the cornea. A selective change of the optical refraction power of the cornea is thereby achieved. This change is localized, i.e. in the area of the cornea from which the tissue volume is removed. The pupil of the eye is usually taken as a basis.

The removal of the cut volume changes the geometry, i.e. the curvature of the cornea surface. In order that a desired correction of defective vision is achieved, the cut volume to be removed must therefore have special properties with regard to its shape.

The cut volume is usually circumscribed by three boundary surfaces, based on classic LASIK methods. An anterior boundary surface is formed at a constant distance under the cornea. This is particularly simple if the cornea is flattened by a flat contact glass. As this cut surface directionally lies furthest forward it is called anterior surface or, on the basis of the known LASIK methods, flap surface.

Furthermore, the volume is limited by a deeper-lying cut surface which is called posterior cut surface or, because the volume can be seen as a lenticle, as lenticle surface. Therefore, it is ensured that overall the volume to be removed changes the curvature of the cornea front surface. One of the two surfaces, usually the posterior one, generally has a geometry which is decisive for correcting defective vision.

In principle, it could be conceived to design the anterior and posterior surfaces such that they have a common cutting line. Firstly, this is not possible when correcting longsightedness as there the volume to be removed must be thinner in the centre, i.e. in the area of the axis of vision, than at the edge. Secondly, when correcting farsightedness it might also be wished, for operational reasons, to ensure a certain minimum thickness of the volume at the edge in order to be able to remove it easily. The anterior surface and the posterior surface are therefore connected via a so-called lenticle edge surface.

SUMMARY

The cut volume is made removable by these three cut surfaces, as the volume is then completely or almost completely enclosed by the cut surfaces. The absolute position and relative extent of the surfaces in the cornea fix the zone within which the optical effect occurs after removal of the cut volume between these surfaces. Here, as already mentioned, the pupil of the eye is usually taken as basis. This approach leads to both cut surfaces, namely the anterior and posterior cut surface, of which one or both can be optically effective, having to be connected to a closed volume which must have a suitable position within the cornea.

The object of the first variant of the invention is to develop a device of the mentioned type or a method of the mentioned type to the effect that control data can be produced for the surgical correction of defective vision with as little computation as possible, and simultaneously, more complex corrections can also be achieved.

This object is achieved according to the invention in the first variant with a device of the type named at the outset in which the radius of curvature $R_{CV}^*$ varies locally and satisfies the following equation:

$$R_{CV}^*(r,\varphi)=1/((1/R_{CV}(r,\varphi))+B_{COR}(r,\varphi)/(n_c-1))+F,$$

wherein $R_{CV}(r,\varphi)$ is the local radius of curvature of the cornea before the volume is removed, $n_c$ is the refractive index of the material of the cornea, F is a coefficient, and $B_{COR}(r,\varphi)$ is the local change in optical refraction power required for the desired correction of defective vision in a plane lying in the vertex of the cornea, wherein there are at least two radii, r1 and r2, for which $B_{COR}(r=r1,\varphi) \neq B_{COR}(r=r2,\varphi)$ holds true.

This object is further achieved according to the invention in the first variant with a method for generating control data for a laser of the type named at the outset, wherein the radius of curvature $R_{CV}^*$ varies locally and satisfies the following equation:

$$R_{CV}^*(r,\varphi)=1/((1/R_{CV}(r,\varphi))+B_{COR}(r,\varphi)/(n_c-1))+F,$$

wherein $R_{CV}(r,\varphi)$ is the local radius of curvature of the cornea before the volume is removed, $n_c$ is the refractive index of the material of the cornea, F is a coefficient, and $B_{COR}(r,\varphi)$ is the local change in optical refraction power required for the desired correction of defective vision in a plane lying in the vertex of the cornea, wherein there are at least two radii, r1 and r2, for which $B_{COR}(r=r1,\varphi) \neq B_{COR}(r=r2,\varphi)$ holds true.

In the first variant, the invention provides a control variable or a reference variable on the basis of which the volume to be removed and thus the cut surface isolating this volume in the cornea can be calculated as precisely as possible. It defines an equation for the radius of curvature which the cornea is to have after the removal of the volume isolated by the treatment device or the method. The volume to be removed can be calculated in an analytically precise manner with this equation.

Upon closer inspection the equation used according to the invention in the first variant to calculate the volume to be removed differs substantially from the approach such as was used in DE 102006053120 A1. A different function is used which no longer takes into account the optical refraction power of spectacles which lie at a distance to the eye, but a distribution of optical refraction power which, written in circular coordinates, varies at least radially. Additionally, this distribution of optical refraction power with which the new radius of curvature which the cornea must have after the surgical correction is calculated no longer lies at a distance from the cornea, but gives the need for correction in a plane which lies in the vertex of the cornea. The invention adopts the analytical approach of DE 102006053120 A1 and simultaneously abandons the spectacle-correction values used there, introducing a radially varying distribution of optical refraction power which reproduces the need for correction of the plane lying in the vertex of the cornea.

Thus, without the calculation effort being significantly increased, a much more extensive correction of defective vision is possible. For example, a correction value which corresponds to the previous spectacle-correction value can now be applied in a central area about the optical axis, e.g. in the radius of the phototopic pupil and other optical refraction power values can be used for greater diameters. Thus a presbyopia of the eye can be dealt with by carrying out in the central area, i.e. in the radius of the phototopic pupil, a correction of near vision (comparable with reading spectacles) and a correction of distant vision (comparable with distance spectacles).

The volume is now determined or can now be determined according to the invention via the equation such that the cornea displays the defined radius of curvature after removal of the volume. A particularly easily calculable and above all also simply achievable (but by no means the only) definition of the volume, limits the volume by a boundary surface which comprises an anterior and a posterior surface part, wherein the anterior surface part lies at a constant distance $d_F$ from the cornea front surface. The terms "anterior" and "posterior" correspond to the usual medical nomenclature. An additional edge surface is necessary (when correcting farsightedness) or advantageous in order to connect the two surface parts and simultaneously guarantee a minimum edge thickness.

Because the anterior surface part is at a constant distance from the cornea surface the formation of this surface part is particularly simple. Naturally, the posterior surface part is then not necessarily at a constant distance from the cornea front surface. The optical correction takes place by shaping the posterior surface part. Calculation effort is considerably simplified by this approach, as a spherical surface part (the anterior surface part) is particularly simple to calculate and the calculation effort is concentrated on the determination of the posterior surface part. With such an approach, the posterior surface part has a curvature pattern which can be identical, apart from an additive constant, to that of the cornea front surface after removal of the volume. The distance between the anterior surface part and the cornea front surface is reflected in the constant.

The radial dependency, present according to the invention in the first variant, of the distribution of optical refraction power means that, viewed in polar coordinates, there are at least two radii for all angles in which there are different values for the distribution of optical refraction power.

The distribution of optical refraction power used may be present as a result of a calculation using wave-front measurement or topography measurement of the cornea front of the cornea. Accordingly, the equation according to the invention on which the calculation of the volume of the cornea is based also provides a local radius of curvature of the cornea. The coordinates system chosen is preferably referenced to the vertex of the cornea.

If the topography $Z_{CV}:R^2 \to R^3$ (quantity of all points $Z_{CV}(r,\varphi)$ which lie on the front of the cornea) is known the local radius of curvature $R_{CV}(z(r,\varphi))$ can be determined for example by a best matching of a sphere surface with the radius R to the surface $Z_{CV}$ in an infinitesimal radius about the point $z_{CV}(r,\varphi)$. The fitting of a curvature circle in radial direction alone can also be used. Then:

$$R_{CV}(r,\varphi) = \frac{\sqrt{1 + \left(\frac{\partial}{\partial r} z_{CV}(r,\varphi)\right)^2}}{\left|\frac{\partial^2}{\partial r^2} z_{CV}(r,\varphi)\right|}$$

In this way the desired distribution of the radius of curvature of the front of the cornea $R_{CV}*(r, \varphi)$, which is to be achieved by the refraction correction $B_{COR}(r, \varphi)$ is obtained by means of the equation according to the invention.

The site-specific refraction correction $B_{COR}(r, \varphi)$ can also be represented in the form of a wave-front. These wave-fronts are often described in practice by Zernike polynomials. In other words, the mathematical description of the refraction correction by locally modifiable optical refraction power forces can be converted directly into a set of Zernike coefficients. Suitable methods for this are known to a person skilled in the art. As an example, reference may be made here to the determination of the spectacle equivalents of the sphere/cylinder/axis from the Zernike coefficient $Z_{2,i}$ and spherical aberration (represented by $Z_{4,0}$). This conversion can be extended analogously to further Zernike orders, which then leads to a general, locally modifiable optical refraction power, also known to specialists as higher-order errors (e.g. coma).

The thickness profile $\Delta z(r,\varphi)$ of the volume to be removed is determined or can be determined according to the invention by the topography $z_{CV}*(r,\varphi)$ of the cornea after the removal of the volume having the local radius of curvature $R_{CV}*(r, \varphi)$ then:

$$z_{CV}*(r,\varphi) = z_{CV}(r,\varphi) - \Delta z(r,\varphi).$$

If an isolated volume is removed from the cornea $\Delta z(r,\varphi)$ is always positive. However, this is not a binding condition for the correction. It is likewise possible to change the refractive correction and, associated with this, the radius of the cornea front side by introducing an additional volume into the cornea. In this case $\Delta z(r,\varphi)$ is always negative. Mixed cases are also possible in which $\Delta z(r,\varphi)$ has both positive and negative areas. In practice this is the case if for example a small refractive correction for distant vision in cases of myopia is to be effected by extraction of tissue and simultaneously a correction of presbyopia by implantation of a small lens in the central area of the optical zone. In this case the thickness of the implant may definitely be greater than the thickness of the volume of tissue to be removed for correcting myopia and thus $\Delta z(r,\varphi)$ have positive values in the central area and negative values in the edge area.

The thickness profile $\Delta z(r,\varphi)$ of the volume results from the difference in topographies. If the desired topography after the correction $z_{CV}*(r,\varphi)$ is known the thickness profile is also determined.

A person skilled in the art can now use analysis or suitable arithmetic methods to determine $z_{CV}*(r,\varphi)$ from $R_{CV}*(r,\varphi)$ by double integration over the surface. The two integration constants occurring are chosen such that for example the desired treatment diameter for refractive correction forms and simultaneously the volume to be removed is minimized.

In particular it is preferred in the first variant that, when determining the control data, the device fixes the local change in optical refraction power $B_{COR}(r,\varphi)$ such that there is a characteristic radius $r_{ch}$ for which the radial function of the change in optical refraction power $B_{COR}(r,\varphi)$ is piecewise constant, for which thus $B_{COR}(r<r_{ch},\varphi=\text{const})=B_a \neq B_b=B_{COR}(r>r_{ch},\varphi=\text{const})$.

The distribution of optical refraction power used for correction can, as already mentioned, have different values in specific areas of the pupil, e.g. a central area as well as an edge area, in order to achieve an optical correction which achieves optimum results even with greatly varying sight conditions or is individually best adapted, e.g. in the case of farsightedness in old age (presbyopia).

In particular it is preferred that, when determining the control data, the device fixes the local change in optical refraction power $B_{COR}(r,\varphi)$ such that there is a characteristic radius $r_{ch}$ for which the radial function of the change in optical refraction power $B_{COR}(r,\varphi)$ is piecewise constant, for which thus $B_{COR}(r<r_{ch},\varphi=\text{const})=B_a \neq B_b=B_{COR}(r>r_{ch},\varphi=\text{const})$.

There can be a continuous transition between the partly constant values of the changes in optical refraction power. For this version it is therefore expedient that, when determining the control data, the device fixes the local change in optical refraction power $B_{COR}(r,\varphi)$ such that there are two radii $r_a$ and $r_b$ for which the radial function of change in optical refraction power $B_{COR}(r,\varphi)$ is piecewise constant, for which thus $B_{COR}(r<r_a,\varphi=\text{const})=B_a \neq B_b=B_{COR}(r>r_b,\varphi=\text{const})$, wherein the radial function of the change in optical refraction power $B_{COR}(r,\varphi)$ passes continuously from $B_a$ to $B_b$ in the transition area between $r_a$ and $r_b$.

The local change in optical refraction power $B_{COR}(r,\varphi)$ can, as special case, have symmetries which make it possible to separate the relationships between coordinates. This makes possible for example the following notations during production of control values:

$B_{COR}(r,\varphi)=B_1(r)B_2(\varphi)$(multiplicative separation approach)

$B_{COR}(r,\varphi)=B_1(r)+B_2(\varphi)$(additive separation approach).

A special case of the separation results if the optical refraction power distribution is not angle-dependent. As this is particularly simple in terms of calculation it is preferred that, when determining the control data, the local change in optical refraction power is or will be fixed in an angle-independent manner.

It should be pointed out quite basically that optical refraction power and radius of curvature can be transformed into each other by a simple equation. Thus: $B=(n_c-1)/R$, wherein B is the optical refraction power and R the radius allocated to this optical refraction power. Thus, within the framework of the invention, it is possible at any time to alternate between radius approach and optical refraction power approach or representation. The equation to be used when determining control data in optical refraction power representations is:

$$B_{CV}^*(r,\varphi) = \frac{1}{\frac{1}{B_{CV}(r,\varphi) + B_{COR}(r,\varphi)} + \frac{F}{(n_c-1)}}$$

When the radius of the cornea surface is mentioned here, the optical refraction power can also be used completely analogously, with the result that all statements made here in connection with the radius of the cornea surface self-evidently also apply analogously to the representation or consideration of the optical refraction power if R is replaced by B according to the named connection.

In the second variant, the object of the invention is to provide, for correction of defective vision by laser surgery in which correction surfaces essential for the correction result are formed as a cut surface in the eye, a method as well as a device for calculating control data with which any correction surfaces can be used and sufficient account is still taken of the influences of a contact glass.

This object is achieved according to a second version of the invention by a method for generating control data which are adapted to control a laser for the surgical correction of the defective vision of an eye of a patient, wherein, during operation of the laser the cornea is deformed by pressing its anterior side against a contact surface, wherein, in the method, a correction surface is predetermined for the non-deformed cornea, which correction surface is to be generated for correction of defective vision as a cut surface in the cornea, and wherein, in the method, during operation of the laser, the deformation of the cornea during operation of the laser is taken into account by a transformation of the coordinates of points in the non-deformed cornea into coordinates of the same points in the deformed cornea, wherein a) several points lying in the correction surface or in an approximation surface derived therefrom are selected and its coordinates transformed by means of the transformation in order to obtain transformed points, b) an interpolation surface is adapted to the transformed points by interpolation and c) target points lying on the interpolation surface (I') are selected and used for generating control data.

This object is further achieved according to the second version of the invention by a device for generating control data which are adapted to control a laser for the surgical correction of the defective vision of an eye of a patient, wherein, during operation of the laser, the cornea is deformed by pressing its anterior surface against a contact surface and wherein a correction surface is predetermined for the non-deformed cornea, which correction surface is to be generated for correction of defective vision as a cut surface in the cornea, and wherein the device, when generating the control data, takes into account the deformation of the cornea during operation of the laser by a transformation of the coordinates for points in the non-deformed cornea into coordinates of the same points in the deformed cornea, wherein a) the device, when generating the control data, selects several points lying in the correction surface or in an approximation surface derived therefrom and transforms its coordinates by means of the transformation in order to obtain transformed points, b) the device, when generating the control data, adapts an interpolation surface to the transformed points by interpolation and c) the device, when generating the control data, selects target points lying on the interpolation surface and uses them to generate the control data.

In the second variant, the invention starts from the situation that the cornea is deformed if the cornea front surface is given a specific shape in that the contact glass mentioned at the outset is pressed against it. Furthermore, the second variant of the invention assumes that the deformation of the cornea can be reproduced by a coordinate transformation which converts the coordinates of points in the non-deformed cornea into transformed coordinates of the same points in the deformed cornea.

Building on these known transformations, the invention provides for any shape of correction surfaces which are to be produced as cut surfaces in the cornea to be treated suitably in order to take into account the effect of cornea deformation. The process according to the second variant of the invention allows any correction surfaces to be treated. In particular, there is no longer a limitation to spherical surfaces such as were previously discussed in the state of the art. As a result, the cornea deformation can also be taken into account for any, particularly non-rotation-symmetrical, cut surfaces. While spherical correction surfaces or correction surfaces which represent a combination of a sphere and a cylinder part (such as are known when correcting astigmatism) can be treated analytically in respect of the coordinate transformation and essentially only the vertex and an edge point for a sphere or two edge points for a combination of sphere and cylinder need be considered in the transformation, such an approach is not possible with correction surfaces which effect higher-order corrections or are also non-rotation-symmetrical. Such correction surfaces can also be treated with the principle according to the invention in respect of cornea deformation.

This process allows any shape of correction surface to be used and still take into account the effect of deformation on the cornea for these correction surfaces. It is also no longer essential to adapt the curvature of the contact glass as precisely as possible to the curvature of the natural cornea in order to minimize errors caused by deformations if the correction surface is to have a shape other than the customary spherical or spherical cylindrical shapes.

Furthermore, the interpolation surface I' obtained by interpolation (or optionally approximation) makes it possible to fix path curves which allow rapid treatment. If, on the other hand, it were wished to transform the target points themselves or a path curve which connects the target points, it would not automatically be ensured that the transformed target points or the transformed path curve would automatically still be optimal with respect to treatment speed. On the basis of the virtually arbitrary distortions which can be caused by the contact pressure transformation, it would be better to assume that the optimum is no longer reached.

Depending on the definition of the correction surface, a really large number of characteristic points may be necessary to be able to carry out the interpolation after the transformation of the characteristic points with sufficient accuracy. In such cases, a further embodiment of the invention may be advantageous which firstly derives an approximation surface from the correction surface. A smoothing process or also an approximation process can be used. The smoothing can in particular be a deep-pass filtering. An approximation by an analytically more easily described approximation surface is also possible. A particular advantage is achieved if an approximation surface is chosen which has a 2-, 3- or 4-fold angle symmetry. The approximation surface, not the correction surface itself, is then subjected to the transformation. In order to take into account the differences between the approximation surface and the correction surface, a deviation between the correction surface and the approximation surface is also determined. This deviation is expediently determined at the characteristic points selected for the transformation. However, it is also possible to determine a general deviation function or a deviation matrix. This deviation, which is not subjected to the transformation, is then used to correct the interpolation surface. This approach thus assumes that the deviation in respect of the transformation is essentially invariant. The computational effort can be considerably reduced in this embodiment.

The points to be selected for the transformation preferably take account of symmetries of the correction surface. Furthermore, it is expedient to take into account invariances of the contact pressure transformation when choosing the points to be transformed which can also be regarded as characteristic points.

The features described here can naturally be combined as desired with one another, providing they do not contradict each other technically. In particular features of the first variant of the invention can be combined with features of the second variant of the invention.

The methods according to the invention of all variants for generating the control data can be carried out without recourse to human involvement. In particular they can be carried out by a computer which carries out the method according to the invention under the control of a program according to the invention and determines the control data for the laser from the corresponding presets. In particular when generating control data there is no need for the participation of a doctor as there is no therapeutic procedure involved in generating the control data. A therapeutic procedure takes place only when the previously determined control data are employed.

Where a method or individual steps of a method for generating control data for surgical correction of defective vision are described in this description, the method or individual steps of the method can be carried out using a correspondingly adapted device. This applies analogously to the explanation of the mode of operation of a device which carries out the method steps. To this extent the device and method features of this description are equivalent. In particular it is possible to realize the method with a computer on which a corresponding program according to the invention is executed.

BRIEF DESCRIPTION OF THE DRAWINGS

The invention is explained in even more detail below, by way of example, with reference to the drawings. There are shown in.

DETAILED DESCRIPTION

Figure 1:
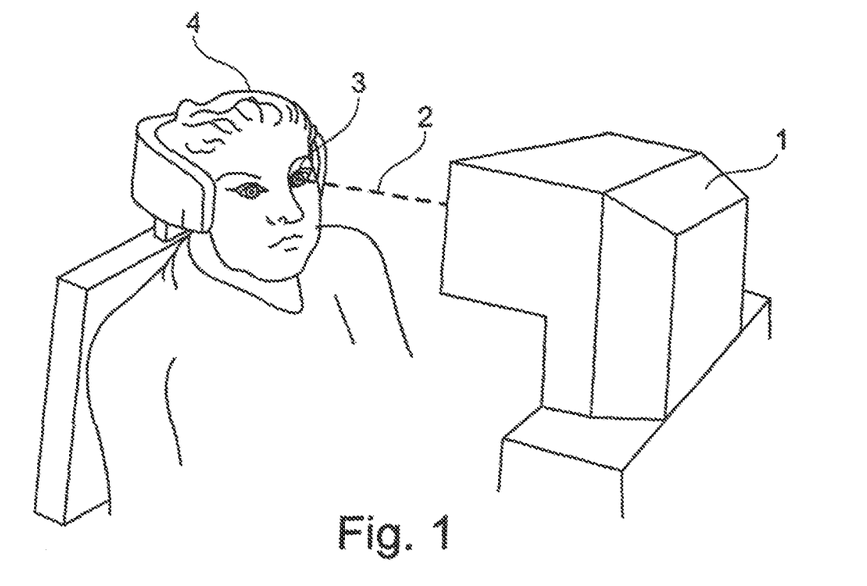
FIG. 1 a schematic representation of a treatment device or of a treatment apparatus for correcting defective vision, FIG. 2 a schematic representation of the structure of the treatment apparatus of FIG. 1, FIG. 3 a presentation showing the principle of introducing pulsed laser radiation into the eye when correcting defective vision with the treatment apparatus of FIG. 1, FIG. 4 a further schematic representation of the treatment apparatus of FIG. 1, FIG. 5 a schematic sectional representation through the cornea showing a volume to be removed for correcting defective vision, FIG. 6 a section through the cornea after removal of the volume of FIG. 5, FIG. 7 a sectional representation similar to that of FIG. 5, FIG. 8 a schematic sectional representation through the cornea to illustrate the volume removal, FIG. 9 a diagram with possible patterns of a distribution of optical refraction power which is used when determining the volume to be removed, FIG. 10 a flowchart for determining the volume to me removed, FIG. 11 a graph illustrating the geometrical transformation method for a specific angle about the z axis and FIG. 12 a graph illustrating a transformation method simplified vis-à-vis FIG. 11.

FIG. 1 shows a treatment apparatus 1 for an eye-surgery procedure which is similar to that described in EP 1159986 A1 or in U.S. Pat. No. 5,549,632. By means of a treatment laser radiation 2 the treatment apparatus 1 effects a correction of defective vision on an eye 3 of a patient 4. Defective vision can include hyperopia, myopia, presbyopia, astigmatism, mixed astigmatism (astigmatism in which there is hyperopia in one direction and myopia in a direction lying at right angles thereto), aspherical errors and higher-order aberrations. In the embodiment described, the treatment laser radiation 2 is applied as a pulsed laser beam focused into the eye 3. The pulse duration in this case is e.g. in the femtosecond range, and the laser radiation 2 acts by means of non-linear optical effects in the cornea. The laser beam has short laser pulses of e.g. 50 to 800 fs (preferably 100-400 fs) with a pulse repetition frequency of between 10 and 500 kHz. In the embodiment described, the modules of the apparatus 1 are controlled by an integrated control unit, which, however, can of course also be formed as a stand-alone unit.

Before the treatment apparatus is used, the defective vision of the eye 3 is measured with one or more measuring devices.

Figure 2:
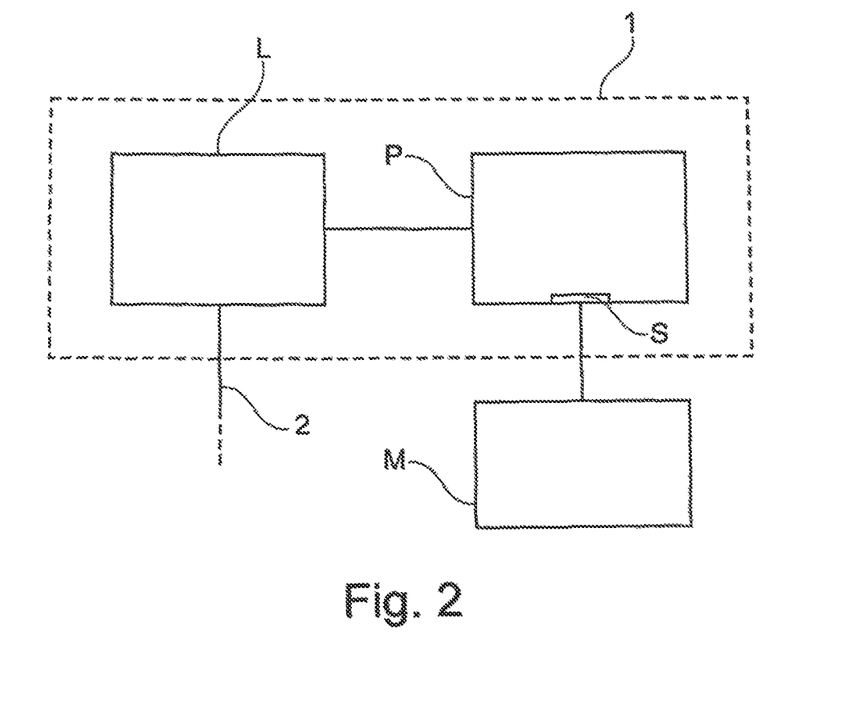

FIG. 2 shows the treatment apparatus 1 schematically. In this variant it has at least two devices or modules. A laser L emits the laser beam 2 onto the eye 3. The operation of the laser L in this case is fully automatic, i.e. in response to a corresponding start signal the laser L starts to deflect the laser beam 2 and thereby produces cut surfaces which, in a manner to be described, are built up and isolate a volume in the cornea. The laser L receives the control data necessary for operation beforehand from a planning device P as a control data set, via control lines that are not described in more detail. The data are transmitted prior to operation of the laser L. Naturally, communication can also take place wirelessly. As an alternative to direct communication, it is also possible to arrange the planning unit P physically separated from the laser L, and to provide a corresponding data transmission channel.

Preferably, the control data set is transmitted to the treatment apparatus 1 and more preferably, the operation of the laser L is blocked until there is a valid control data set at the laser L. A valid control data set can be a control data set which in principle is suitable for use with the laser L of the treatment device 1. Additionally, however, the validity can also be linked to the passing of further tests, for example whether details, additionally stored in the control data set, concerning the treatment apparatus 1, e.g. an appliance serial number, or concerning the patient, e.g. a patient identification number, correspond to other details that for example have been read out or input separately at the treatment device as soon as the patient is in the correct position for the operation of the laser L.

The planning unit P produces the control data set that is made available to the laser unit L for carrying out the operation from measurement data and defective-vision data which have been determined for the eye to be treated. They are supplied to the planning unit P via an interface S and, in the embodiment example represented, come from a measuring device M which has previously taken measurements of the eye of the patient 4. Naturally, the measuring device M can transfer the corresponding measurement and defective-vision data to the planning device P in any desired manner.

Transmission can be by means of memory chips (e.g. by USB or memory stick), magnetic storage (e.g. disks), by radio (e.g. WLAN, UMTS, Bluetooth) or wired connection (e.g. USB, Firewire, RS232, CAN-Bus, Ethernet etc.). The same naturally also applies with regard to the data transmission between planning device P and laser L.

A direct radio or wired connection of measurement device M to treatment device 1 with regard to data transfer which can be used in a variant has the advantage that the use of incorrect measurement and defective-eye data is excluded with the greatest possible certainty. This applies in particular if the patient is transferred from measuring device M or measuring devices to the laser L by means of a storage device (not represented in the Figure) which interacts with measuring device M or laser L such that the respective devices recognize whether the patient 4 is in the respective position for measurement or introduction of the laser radiation 2. By bringing the patient 4 from measuring device M to laser L the transmission of measurement and error-correction data to the treatment device 1 can also take place simultaneously.

Preferably it is ensured by suitable means that the planning device P always produces the control data set belonging to the patient 4 and an erroneous use of a false control data set for a patient 4 is as good as excluded.

Figure 3:
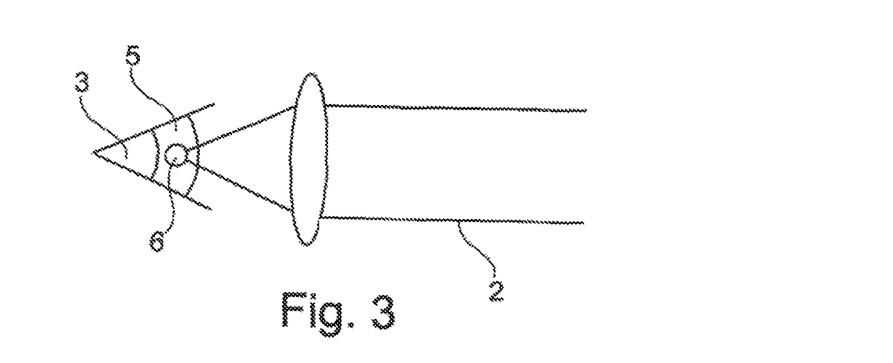

The mode of operation of the laser beam 2 is indicated schematically in FIG. 3. The treatment laser beam 2 is focused into the cornea 5 of the eye 6 by means of a lens which is not shown in more detail. As a result there forms in the cornea 5 a focus that covers a spot 6 and in which the energy density of the laser radiation is so high that, in combination with the pulse length, a non-linear effect in the eye results. For example, each pulse of the pulsed laser radiation 2 can produce at the respective spot 6 an optical break-through in the cornea 5 which, in turn, initiates a plasma bubble, indicated schematically in FIG. 3. As a result, tissue in the cornea 5 is cut disrupted this laser pulse. When a plasma bubble forms, the tissue layer disruption covers a larger region than the spot 6 covered by the focus of the laser radiation 2, although the conditions for producing the break-through are achieved only in the focus. In order for an optical break-through to be produced by every laser pulse, the energy density, i.e. the fluence, of the laser radiation must be above a certain threshold value which is dependent on pulse length. This relationship is known to a person skilled in the art from, for example, DE 69500997 T2.

Alternatively, a tissue-cutting effect can also be produced by the pulsed laser radiation by sending several laser radiation pulses into a region, wherein the spots 6 overlap for several laser radiation pulses. Several laser radiation pulses then act together to achieve a tissue-cutting effect.

The type of tissue cutting which the treatment apparatus 1 uses is, however, no further relevant for the description below, although pulsed treatment laser radiation 2 is described in this description. For example a treatment apparatus 1 such as is described in WO 2004/032810 A2 can be used. A large number of laser-pulse foci forms a cut surface in the tissue, the form of which depends on the pattern with which the laser-pulse foci are/become arranged in the tissue. The pattern specifies target points for the focus position at which one or more laser pulse(s) is (are) emitted and defines the form and position of the cut surface.

In order now to carry out a correction of defective vision, material is removed from a region within the cornea 5 by means of the pulsed laser radiation by cutting tissue layers thus isolating the material and then make it possible for material to be removed. The removal of material effects a change in the volume of the cornea which results in a change in the optical imaging effect of the cornea 5, which change is calculated exactly such that the previously determined defective vision thus is/becomes corrected as much as possible. To isolate the volume to be removed, the focus of the laser radiation 2 is directed towards target points in the cornea 5, generally in an area which is located beneath the epithelium and the Bowman's membrane and above the Decemet's membrane and the endothelium. For this purpose the treatment apparatus 1 has a mechanism for shifting the position of the focus of the laser radiation 2 in the cornea 5. This is shown schematically in FIG. 3.

Figure 4:
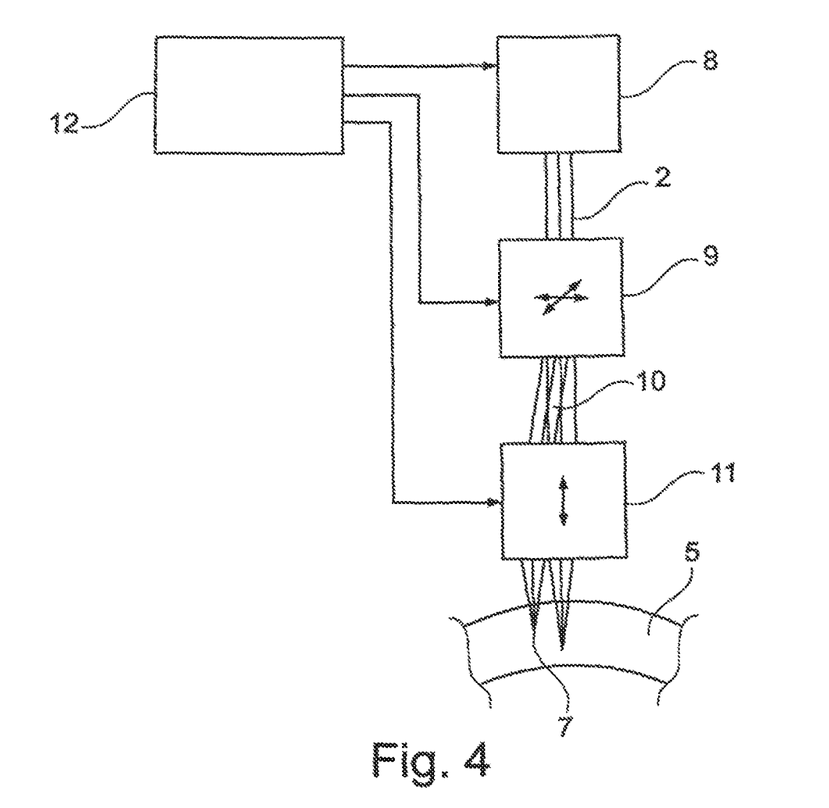

In FIG. 4, elements of the treatment apparatus 1 are shown only as long as they are necessary to understand the shifting of the focus. As already mentioned, the laser radiation 2 is bundled in a focus 7 in the cornea 5, and the position of the focus 7 in the cornea is shifted such that, to produce cut surfaces, energy from laser radiation pulses is introduced into the tissue of the cornea 3 focused at various points. The laser radiation 2 is provided by a laser 8 as pulsed radiation. An xy scanner 9 which, in one variant, is realized by two substantially orthogonally deflecting galvanometric mirrors, deflects the laser beam of the laser 8 in two dimensions such that there is a deflected laser beam 10 after the xy scanner 9. The xy scanner 9 thus effects a shifting of the focus 7 substantially perpendicular to the main direction of incidence of the laser radiation 2 into the cornea 5. To adjust the depth position a z scanner 11 which is realized, for example, as an adjustable telescope, is provided in addition to the xy scanner 9. The z scanner 11 ensures that the z position of the focus 7, i.e. its position on the optical incidence axis, is changed. The z scanner 11 can be arranged before or after the xy scanner 9. The coordinates designated x, y, z in the following thus relate to the deflection of the position of the focus 7.

The allocation of the individual coordinates to the spatial directions is not essential for the operating principle of the treatment apparatus 1; but to simplify the description, in the following the coordinate along the optical axis of incidence of the laser radiation 2 is always designated z, and x and y designate two coordinates orthogonal to one another in a plane perpendicular to the direction of incidence of the laser beam. It is naturally known to a person skilled in the art that the position of the focus 7 in the cornea 5 can also be described three-dimensionally by other coordinate systems, in particular that the coordinate system need not be a rectangular system of coordinates. Thus it is not essential for the xy scanner 9 to deflect around axes that are at right angles to one another; rather, any scanner capable of shifting the focus 7 in a plane in which the incidence axis of the optical radiation does not lie can be used. Oblique-angled coordinate systems are thus also possible.

Further, non-Cartesian coordinate systems can also be used to describe, or control, the position of the focus 7, as will also be explained further below. Examples of such coordinate systems are spherical coordinates as well as cylindrical coordinates.

To control the position of the focus 7, the xy scanner 9 as well as the z scanner 11, which together realize a specific example of a three-dimensional focus-shifting device, are controlled by a control apparatus 12 via lines not described in more detail. The same applies to the laser 8. The control apparatus 3 ensures a suitably synchronous operation of the laser 8 as well as the three-dimensional focus-shifting device, realized by way of example by the xy scanner 9 and the z scanner 11, with the result that the position of the focus 7 is shifted in the cornea 5 such that, ultimately, a specific volume of material is isolated, wherein the subsequent volume removal effects a desired correction of defective vision.

The control apparatus 12 operates according to predetermined control data which predetermine the target points for shifting the focus. The control data are generally collected in a control data set. In one embodiment, this predetermines the coordinates of the target points as a pattern, wherein the sequence of the target points in the control data set fixes the serial arrangement of the focus positions alongside one another and thus, ultimately, a path curve (also referred to here in short as a path). In one embodiment, the control data set contains the target points as specific reference values for the focus-shifting mechanism, e.g. for the xy scanner 9 and the z scanner 11. To prepare the eye-surgery procedure, thus before the actual operation can be carried out, the target points and preferably also their order are determined in the pattern. There must be pre-planning of the surgical procedure to determine the control data for the treatment apparatus 1, the application of which then achieves an optimal correction of defective vision for the patient 4.

Firstly, the volume to be isolated in the cornea 5 and later removed must be defined. As already described with reference to FIG. 2 this requires to establish the need for correction.

With regard to the nomenclature used in this description it may be noted that the addition of an asterisk to values indicates that these are values which are obtained after a correction. On the justified assumption that a change in thickness of the cornea 5 substantially modifies the radius of curvature of the front face 15 of the cornea facing the air, but not the radius of curvature of the rear 16 of the cornea adjacent to the inside of the eye, the radius of curvature $R_{CV}$ of the front of the cornea 15 is modified by the volume removal. Because of the modified curvature of the front having changed cornea surface 15*, the cornea 5 reduced by the volume has a correspondingly modified imaging effect, with the result that there is now a corrected focus on the retina 14.

To determine the pattern of the target points, the curvature to be achieved $R_{CV}^*$ of the cornea front surface 15* is therefore determined.

Using the value $B_{COR}$, the curvature of the modified cornea front surface 15* is now set as follows:

$$R_{CV}^*(r,\varphi)=1/((1/R_{CV}(r,\varphi))+B_{COR}(r,\varphi)/(n_c-1))+F, \qquad (1)$$

In equation (1) $n_c$ denotes the optical refraction power of the material of the cornea. The proper value is usually 1.376; $B_{COR}$ denotes a change in optical refraction power which is necessary to correct defective vision. $B_{COR}$ is radially dependent. By radial dependence is meant that there are two values r1 and r2 for the radius r for which the change in optical refraction power has different values at all angles $\varphi$.

Figure 9:
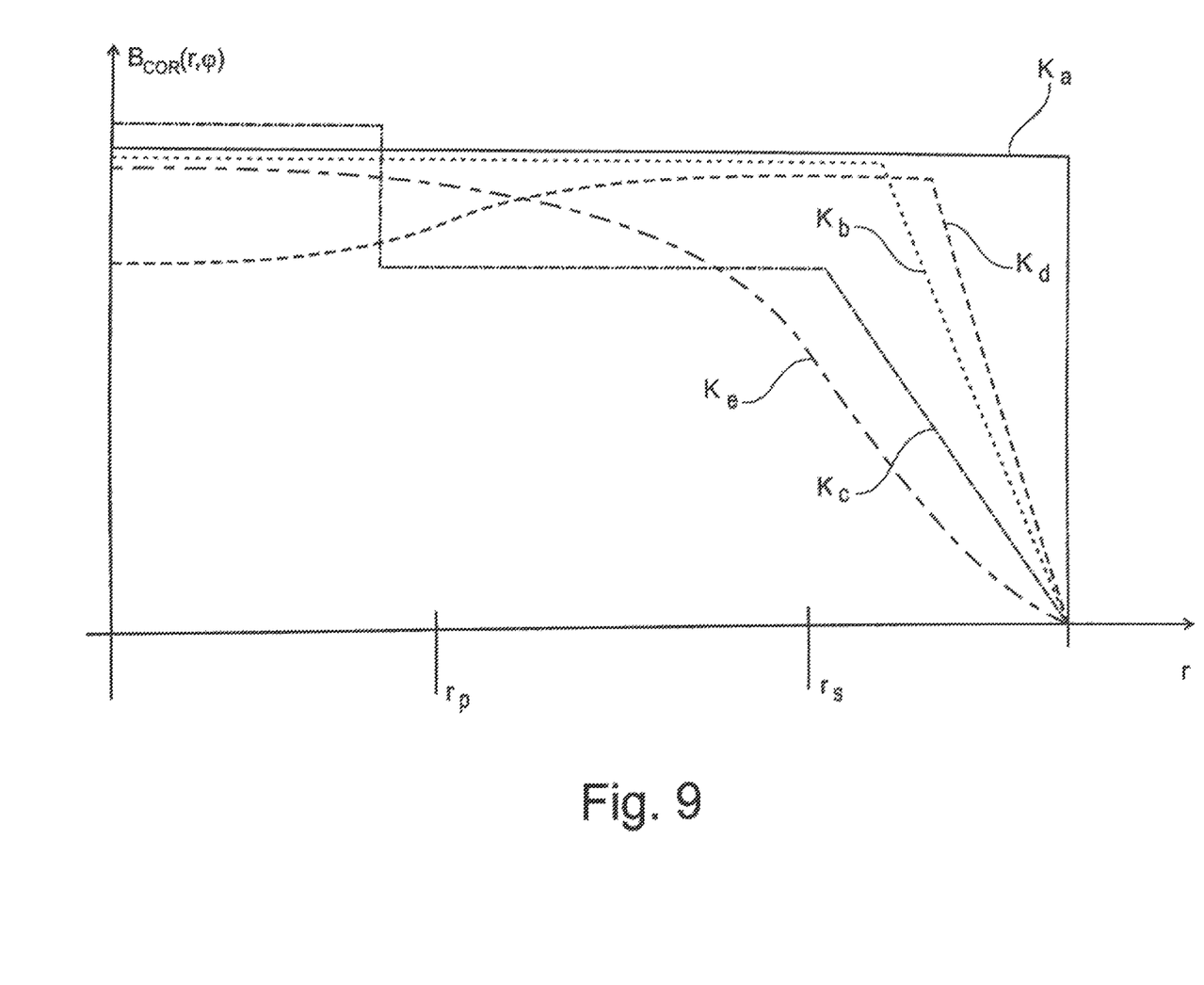

Examples of possible patterns of changes in optical refraction power are shown by way of example in FIG. 9 which shows the function $B_{COR}$ in different exemplary curves Ka to Ke as a function of the radius r.

Ka is the conventional refractive index of spectacles from the state of the art according to DE 102006053120 A1, but already referenced to the plane of the vertex of the cornea in the representation of FIG. 9. In the cited state of the art there is no reason for such reference relationship. It has been included here only for the purpose of better comparability with the exemplary curves Kb to Ke according to the invention. The curve Kb is constant up to a radius which lies beyond a radius $r_s$, and then falls. The radius $r_s$ is thus the scotopic pupil radius, i.e. the pupil radius at night vision. The change in optical refraction power according to curve Kc is partly constant as far as radius $r_s$, wherein below a radius $r_p$, which corresponds to the photopic pupil radius, there is a sudden drop from a higher value to a lower value. Such a variation of the correction in optical refraction power over the cross-section of the pupil is particularly advantageous in the case of farsightedness in old age. Near vision usually occurs under good lighting, e.g. when reading. The pupil is then generally contracted to the photopic pupil radius because of the good lighting. The correction in optical refraction power then necessary sets an optimum adaptation to near vision, e.g. an optimum viewing distance of approximately 25 to 70 cm. For the other extreme case, namely night vision, which is usually linked with looking into the distance (e.g. when driving at night), on the other hand, the pupil is opened to its maximum. Then, areas of the pupil which have a different (e.g. lower) value for correcting optical refraction power also contribute to optical imaging. The human brain is capable of correcting imaging having such visual errors (different position of focus for the centre of the pupil and edge areas of the pupil) in visual perception. The correction of optical refraction power curves shown in the curves Kc or Kd thus allow, consciously accepting an imaging error, the enlargement of the focus depth range, as the imaging error is compensated for by the brain.

The correction of optical refraction power then drops again from pupil radius $r_s$. The unstepped drop in the correction of optical refraction power to zero is advantageous from an anatomical point of view. It allows, at the edge of the corrected range, i.e. at the edge of the volume to be removed, an adaptation of the corrected cornea front radius which is set, on the basis of the correction, to the original radius of curvature of the cornea, i.e. the pre-operative radius. Reverting to the representation of FIG. 5 this means that there is an adjustment of these radii in the edge area of the volume to be removed at which the radii $R_F$ and $R_L$ converge in the representation of FIG. 5. As a result, the transition from the new cornea front-side radius $R_{CV}^*$ which occurs in the area in which the volume 18 has been removed to the original radius of curvature of the cornea $R_{CV}$ is comparably soft. The optical correction is thus overall better, which can be achieved only because of the radially varying the correction of optical refraction power.

The drop in the correction of optical refraction power to zero takes place preferably in an area outside the darkened pupil radius, thus in an area of the cornea no longer relevant for vision.

The curve Kd shows a similar pattern, but here there is a smooth transition from the first value of the change in optical refraction power below $r_p$ to the second value at $r_s$. Also, by way of example, the first value here is lower than the second value. This can naturally also be used for the curve Kc, depending on the desired requirement for correction. Curve Ke shows a continuous decline.

The locally varying changes in optical refraction power, described with reference to FIG. 9, with radial dependence, are examples of a change in optical refraction power which is used when determining the volume to be removed in the operation.

The coefficient F expresses the optical effect of the change in thickness which the cornea experiences as a result of the surgical procedure and can be seen in a first approximation as a constant coefficient which can be determined e.g. experimentally in advance. For a highly accurate correction the coefficient can be calculated according to the following equation:

$$F=(1-1/n_c)\cdot\Delta z(r=0,\varphi) \qquad (2)$$

$\Delta z(r=0, \varphi)$ is the central thickness of the volume to be removed.

For a precise determination, $R_{CV}^*$ is iteratively calculated by determining in an nth calculation step the value $\Delta z(r=0,\varphi)$ from the difference $1/R_{CV}*(r=0,\varphi)-1/R_{CV}\Delta r=0,\varphi)$ and using the corresponding result obtained from this for the change in thickness in the (n+1)th calculation step as new value for $R*_{CV}$. This can be carried out until an abort criterion is met, for example if the difference in the result for the change in thickness in two successive iterations lies below a suitably fixed limit. This limit can for example be set as a constant difference which corresponds to an accuracy of the refraction correction that is appropriate to the treatment.

Figure 10:
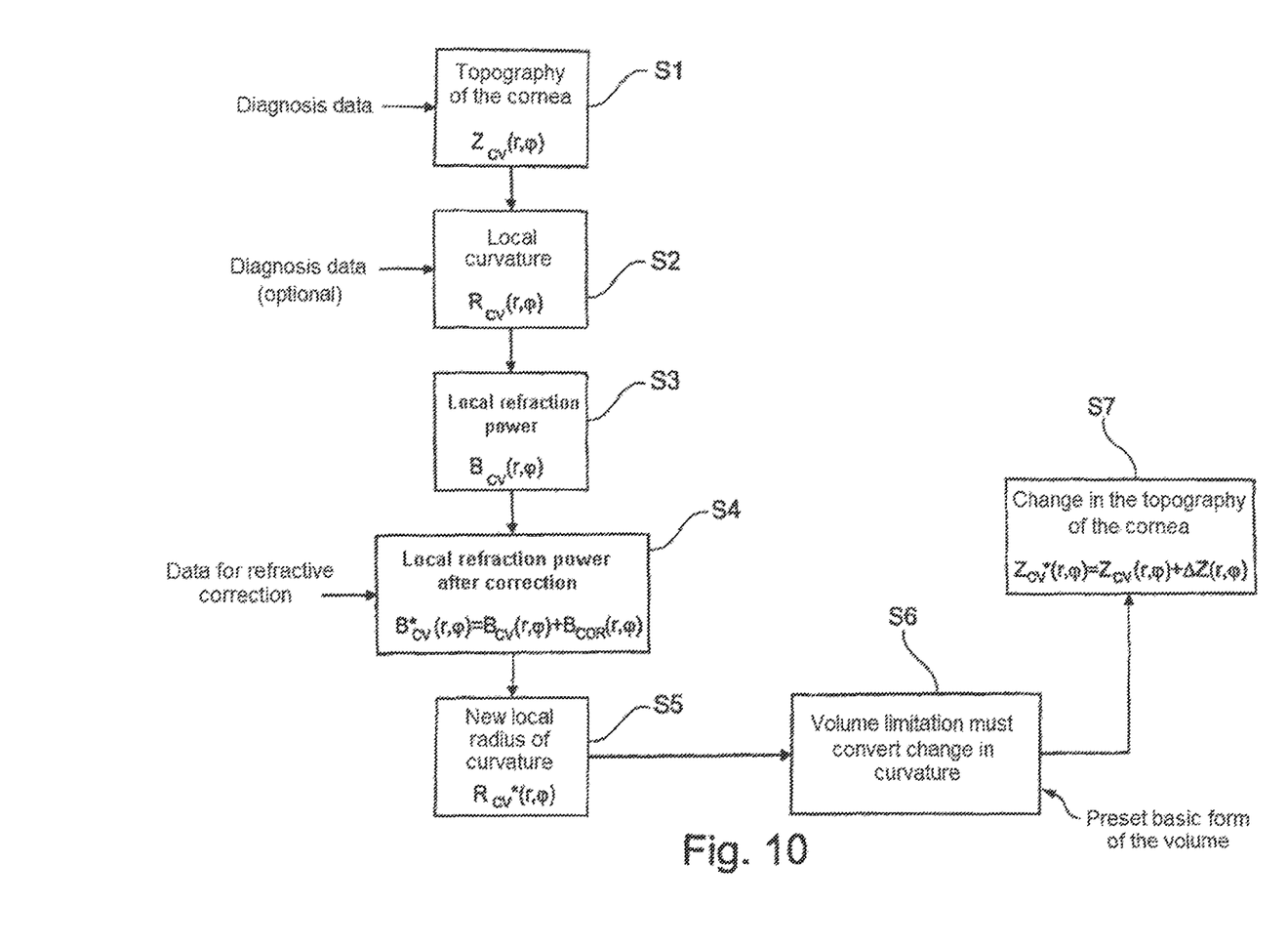

In general the method represented in FIG. 10 can be carried out. In a step S1 the topography of the cornea is calculated from diagnosis data, as mentioned already at the start in the general section of the description. The radial curvature of the front 15 of the cornea is determined from this topography. This can also be directly determined from the diagnosis data, instead of the topography data from step S1, with the result that step S2 is either placed after step S1 or diagnosis data are directly evaluated as FIG. 10, shows by adding "(optional)". Thus step S1 is optional.

Typical diagnosis data for step S2 are measurement data which describe the site-specific curvature of the cornea, for example the topography data of cornea topographs (Scheimpflug, Placido projectors) or simple keratometers which determine only the average curvature of the cornea on the steepest and flattest meridian. It is likewise possible that the global curvature of the cornea is used as manual input parameter or that even a fixed value is used if no specific adaptation appears necessary.

The local optical refraction power of the cornea is determined in a step S3.

The required local change in optical refraction power $B_{COR}$ is determined from data relating to the desired refractive correction in a step S4 and the local optical refraction power desired after the correction determined from this local change in optical refraction power. The desired refractive correction can then be input directly as locally varying optical refraction power or, as mentioned initially, equivalently also in the form of a general wave-front change which can then be represented for example in the form of Zernike coefficients.

If the locally varying optical refraction power is used, there is thus a particularly descriptive presentation if, instead of a local optical refraction power at a specific point, the average of the optical refraction power over a ring segment, in particular over a circular surface, is displayed and entered.

It is likewise possible to incorporate diagnosis data concerning the preoperative wave-front in order to derive the wave-front changes to be realized, which in turn leads to a specific target wave-front. Mixed forms in which the data of the subjectively determined refraction values sphere/cylinder/axis are combined with the wave-front measurement data are also possible.

The new local radius of curvature $R*_{CV}(r,\varphi)$ is generated then in step S5. Instead of the calculation of the local optical refraction power $B_{CV}$ in step S3, calculation can also take place directly with the local curvature $R_{CV}$ from step S2 if the above equation (1) is used. It should be pointed out quite basically that optical refraction power and radius of curvature can be transformed into each other by a simple equation. Thus: $B=(n_c-1)/R$, wherein B is the optical refraction power and R the radius allocated to this optical refraction power. Thus, within the framework of the invention, it is possible at any time to alternate between radius approach and optical refraction power approach or representation. The equation to be used when determining control data in optical refraction power representations is:

$$B^*_{CV}(r,\varphi) = \frac{1}{\frac{1}{B_{CV}(r,\varphi)+B_{COR}(r,\varphi)} + \frac{F}{(n_C-1)}}$$

When the radius of the cornea surface is mentioned here, the optical refraction power can also be used completely analogously, with the result that all statements made here in connection with the radius of the cornea surface self-evidently also apply analogously to the representation or consideration of the optical refraction power if R is replaced by B according to the named dependency.

For the volume whose removal effects the above change in curvature of the cornea front surface 15 the boundary surface isolating the volume is now defined in a step S6. Account is to be taken of what basic form the volume is to have.

In a first variant by numerical methods known to a person skilled in the art a free from surface is defined which circumscribes the volume whose removal effects the change in curvature. The volume thickness required for the desired modification in curvature is determined along the z axis. This gives the volume a function of r, $\varphi$ (in cylinder coordinates) and the boundary surface is defined based on the volume.

Figure 5:
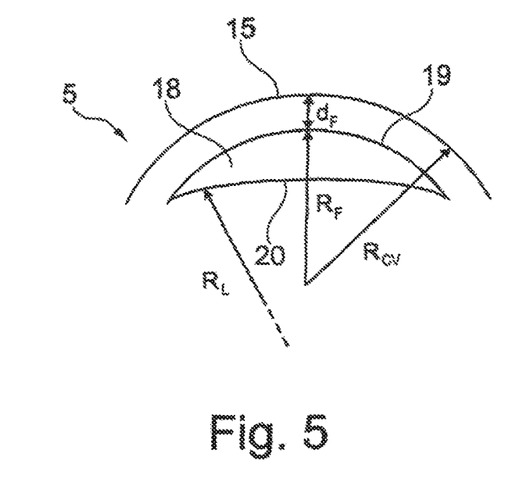

On the other hand an analytical calculation is delivered by the following variant, already discussed in DE 102006053120 A1, in which the boundary surface of the volume is essentially built up from two surface parts, an anterior surface part facing the cornea surface 15 and an opposite posterior surface part. FIG. 5 shows the corresponding relationships. The volume 18 is limited towards the cornea front 15 by an anterior cut surface 19 which is at a constant distance $d_F$ below the cornea front surface 15. This anterior cut surface 19 is also called flap surface 19 by analogy with the laser keratomes as it serves, in combination with an opening section 22 towards the edge, to be able to raise a flap-shaped lamella from the cornea 5 from the cornea 5 beneath. This way of removing the previously isolated volume 18 is naturally possible here also.

The anterior cut surface 19 is preferably spherical as then a radius of curvature which is smaller by the thickness of a lamella $d_F$ than the radius of curvature $R_{CV}$ can be defined.

To the rear the volume 18 which is to be removed from the cornea 5 is limited by a posterior cut surface 20 which already basically cannot be at a constant distance from the cornea front surface 15. The posterior cut surface 20 is therefore formed such that the volume 18 has the form of a lenticle, which is why the posterior cut surface 20 is also called lenticle surface. This surface is shown in FIG. 5 by way of example as a likewise spherical surface with a radius of curvature $R_L$, wherein in FIG. 5 naturally the center of this curvature does not coincide with the center of curvature of the likewise spherical cornea front surface 15. The two surfaces 19, 20 are preferably connected at their edge by a lenticle edge surface in order to completely circumscribe the volume to be removed and simultaneously guarantee a minimum thickness at the edge.

Figure 6:
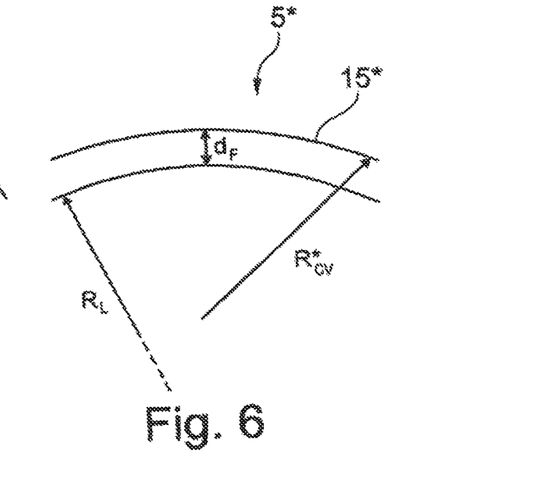
Figure 7:
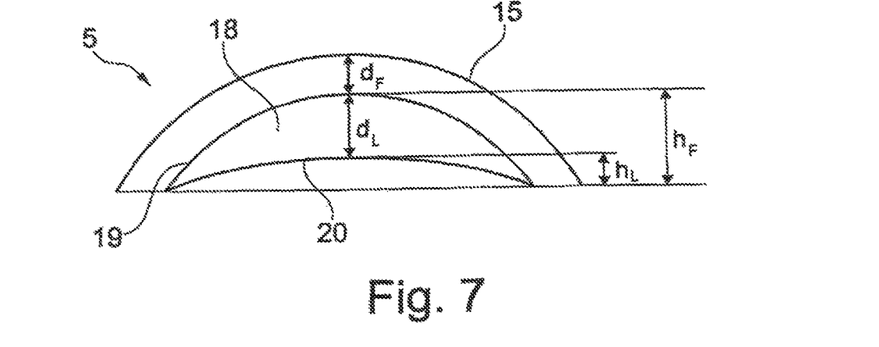
Figure 8:
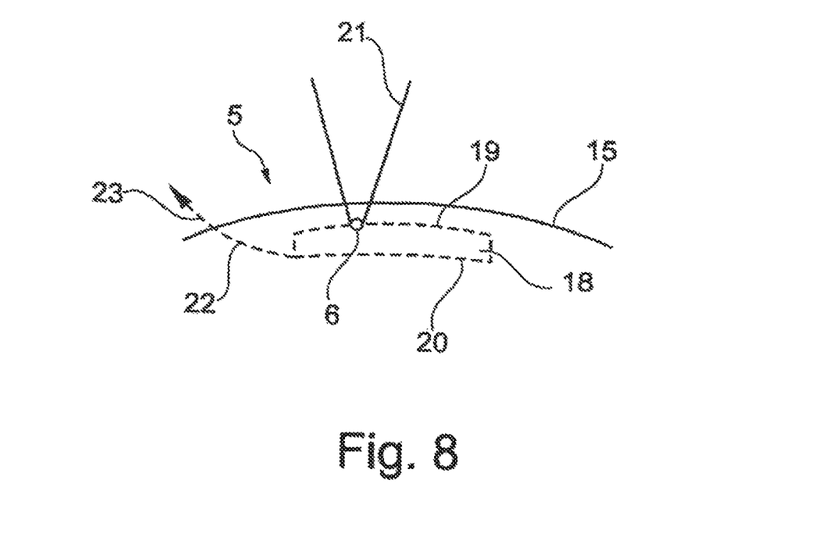

FIG. 6 shows the situation after the volume 18 has been removed. The radius of the modified cornea front surface 15* is now $R_{CV}*$ and can for example be calculated according to the previously described equations. The thickness $d_L=\Delta z(r=0,\varphi)$ of the removed volume 18 governs the change in radius, as illustrated by FIG. 7. The lenticle surface is simplified to be spherical in this figure. Consequently, the height $h_F$ of the ball cap defined by the flap surface 19, the height $h_L$ of the ball cap defined by the lenticle surface 20 and the thickness dL of the volume 18 to be removed are shown.

Due to the constant distance between cornea front surface 15 and flap surface 19, the lenticle surface 20 defines the curvature of the cornea front surface 15* after the volume 18 has been removed.

If the coefficient F is to be taken into account during calculation, in step S7 the change in topography of the cornea are considered, too, i.e. the current central thickness is computed. Using the resulting value for the coefficient F, steps S4 to S6 or S5 to S6 can then be carried out once again or repeatedly in the form of an iteration.

The formation shown in the figures of the volume 18, as limited by a flap surface 19 at a constant distance from the cornea front surface 15 and a lenticle surface 20, is only one variant for limiting the volume 18. However, it has the advantage that the optical correction is given essentially by only one surface (the lenticle surface 20), with the result that the analytical description of the other surface part of the boundary surface is simple.

Furthermore, safety margins with regard to the distance between the volume and cornea front surface 15 and cornea back surface 16 are optimal. The residual thickness $d_F$ between flap surface 19 and cornea front surface 15 can be set to a constant value, e.g. 50 to 200 µm. In particular it can be chosen such that the pain-sensitive epithelium remains in the lamella which is formed by the flap surface 19 beneath the cornea front surface 15. The formation of the spherical flap surface 19 is also continuous with previous keratometer sections which is advantageous in terms of acceptance of the method.

After producing the cut surfaces 19 and 20 the thus-isolated volume 18 is then removed from the cornea 5 in the direction of arrow 23. This is represented schematically in FIG. 9 which also shows that the cut surfaces 19 and 20 are produced by the action of the incident treatment laser beam by exposure to a focus sphere 21, for example by the arrangement of plasma bubbles alongside one another, with the result that in a preferred embodiment the flap surface 19 and the lenticle surface 20 are produced by suitable three-dimensional shifting of the focus position of the pulsed laser radiation 2.

Alternatively in a simplified embodiment, however, merely the flap surface 19 can also be formed, by means of pulsed laser radiation, by target points which define the curved cut surface 19 at a constant distance from the cornea front surface 15, and the volume 18 is removed by laser ablation, for example by using an excimer laser beam. For this, the lenticle surface 20 can be defined as boundary surface of the area removed, although this is not essential. The treatment apparatus 1 then operates like a known laser keratome, but the cut surface 19 is produced using curved cornea. The previously or subsequently described features are also possible in such variants, in particular as regards the determination of the boundary surface, its geometric definition and determining control parameters.

If both the lenticle surface 20 and the flap surface 19 are produced by means of pulsed laser radiation it is expedient to form the lenticle surface 20 prior to the flap surface 19, as the optical result is better with the lenticle surface 20 (if not achievably only then) if there has still been no change in the cornea 5 above the lenticle surface 20.

As already explained in the general section of the description, both the exact positioning of the cornea and also precise knowledge of the curvature of the cornea are essential for the correction of defective vision described here. Only with knowledge of this curvature can for example the described flap section be produced and the desired correction surface as a cut surface in the form of the lenticle surface be achieved.

Therefore a contact glass is used which has a curved contact surface. The cornea is pressed against this. This process leads, as already described initially, to a deformation of the cornea.

If a correction surface has been determined which is to be produced in the eye as a cut surface, this correction surface naturally relates to the non-deformed cornea. However, the cut surface is produced in the deformed cornea, with the result that the correction surface or the cut surface must be modified accordingly before finalizing the control data. This modification considers a predistortion of the correction surface or of the cut surface to be produced, wherein the surface is changed such that, after removing the contact glass, i.e. after the relaxation of the deformation, the desired surface shape is still achieved.

This predistortion of the predetermined correction surface is carried out by subjecting the predetermined correction surface to a coordinate transformation which reproduces the deformation of the cornea. Such coordinate transformations are known from US 2007/0293851 A1, which is incorporated in full in this respect into this disclosure, and also from DE 102008017293 A1, the disclosure of which is likewise incorporated in full.

As explained above, the locally modifiable refractive correction $B_{COR}(r, \varphi)$ is achieved by disrupting tissue layers in the cornea by means of pulsed laser radiation along cut surfaces $F:=z(r,\varphi): R^2 \rightarrow R^3$, with the result that a volume is enclosed which is then removed. The shape of the front surface of the cornea is selectively changed as a result of this step such that the desired correction is obtained. For this, for example, a treatment beam is focussed into the cornea of the eye 6.

The shape $F_A:=z_A(r, \varphi)$ of the anterior cut surface 19 and the shape $F_P:=z_P(r, \varphi)$ of the posterior cut surface 20 of the volume 18 to be removed are essentially determined in that the thickness profile $\Delta z(r,\varphi)=z_A(r,\varphi)-z_P(r, \varphi)$ of the circumscribed material results in the required change in shape of the cornea front surface 15 after removal. Therefore, an exact, absolute positioning of the individual laser shots in the micrometers range within the cornea 5 of the eye to be treated is essential in order to guarantee the accuracies of the refractive correction, which is why the position of the cornea is fixed relative to the optical system of laser radiation, and the cornea front surface 15 is changed into a known shape by pressing the contact glass against the cornea 5 of the eye and e.g. mechanically fixing it there by means of suction (cf. US 2008/234707 A1).

The contact glass changes the shape of the cornea front surface. The deformation is described in US 2007/0293851 with reference to FIGS. 11-13 and is called contact pressure transformation ($AT: R^3 \rightarrow R^3$). As also in the incorporated published documents, variables which relate to the transformed coordinate system are characterized in this description by a superscript.

A correction surface which is also to be produced as a cut surface in the eye is determined for the correction of defective vision. Optionally there can also be more than one surface. By correction surface is meant here any cut surface which must be produced in the eye and which is effective for altering refraction in the eye. For example, the flap surface is not included and the above-described embodiment which concentrates the optical correction in a single surface, namely the lenticle surface, is preferred. The correction surface can be determined in any manner, for example using the principles named above. The 3-dimensional cut surfaces are generated e.g. by arranging individual laser beams alongside one another along a path curve to form cut lines and by arranging cut lines alongside one another to form cut surfaces.

This correction surface is now subjected to the coordinate transformation, as will be explained below.

In the case of more elaborate corrections, in particular in the case of corrections which are not limited to a correction surface, which can be indicated by a sphere or optionally a sphere with a cylindrical portion, the correction surface can pose significant numeric problems if the control data were produced first and then subjected to transformation. As in a system operating with pulsed laser radiation the extent of the physical tissue disruption of an individual laser beam lies in the range of a few square micrometers and the whole cut surface is in the range of approx. 50 mm$^2$, the coordinates of approximately 10 million points would have to be transformed.

In order to avoid this outlay on computation, only a subset, several times smaller, of the points of the correction surface or cut surface, is selected as points $f_i$ of the surface F. The selection of the points preferably takes into account geometric properties of the cut surface F which is to be produced in the non-deformed cornea. Preferably, any symmetries of the cut surface as well as an invariance of the angle imaging in the contact pressure transformation (angle about the optical axis) are taken into account when choosing the points.

Once a subset of the possible points of cut surface F has been selected in this way, these points are transformed with the contact pressure transformation. An interpolation surface I' is then adapted by interpolation. This corresponds with sufficient precision to the transformed correction surface F. The target points and the path(s) containing same which form part of the control data of the treatment device are then fixed in the interpolation surface I'.

The method thus provides the following:

If the scanning device is later controlled such that every single focus point for producing the cut surface lies on the transformed cut surface $F':=z'(r,\varphi)$, the correct volume has been enclosed, as the removal of the contact glass leads to a relaxation of the cornea which corresponds to a retransformation. Thus the following occurs:

1. Characteristic points $f_i$ are selected on the correction surface F and transformed into $f_i'$. The points $f_i$ are preferably chosen such that they represent geometric properties of the cut surface F in the non-deformed cornea 5 (thus in the natural system). Advantageously, the symmetries of the cut surface F are considered. It is also advantageous to take into account invariance of the angle imaging in the contact pressure transformation (angle about the optical axis) when choosing the points.

2. An interpolation surface I' is adapted to the transformed points $f_i'$. Preferably, it is ensured that the symmetry properties of the surface I' deviate only slightly, if at all, from the cut surface F in the non-transformed system.

3. It is further advantageous to adapt the interpolation surface I' to the transformed characteristic points $f_i'$ such that one of the parameters describing the surface is the height z or a parameter which is a substitute in a known relationship to the height z, for which thus a representation such as for example $I':=r(z,\varphi)$ or $I':=y(z,x)$ applies. It is thereby easier to find a path curve for the target points which can be worked along as quickly as possible.

Figure 11:
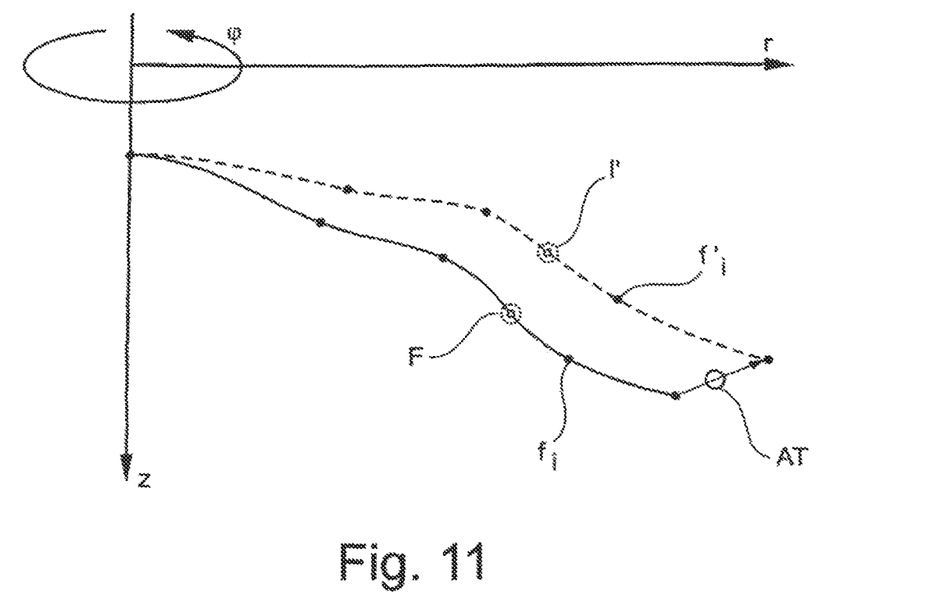

FIG. 11 shows a graphic illustration of the first method for a specific angle about the z axis. FIG. 11 shows by way of example a sectional representation through a correction surface F in the coordinates z and r. The angle $\varphi$ of the cylinder coordinates corresponds to a rotation of the r axis about the z axis. Points $f_i$ are then selected for the surface F as characteristic points which are then transformed into points $f_i'$ with the contact pressure transformation AT. The interpolation surface I' is then defined by the transformed points $f_i'$. This interpolation surface I' then serves to determine the control data.

Figure 12:
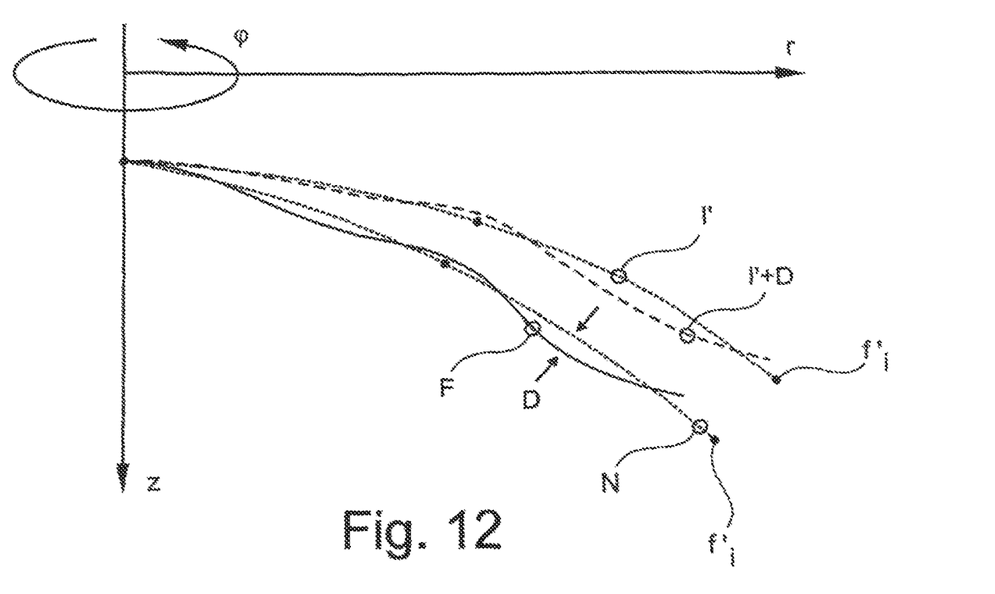

However, the concept of the characteristic points $f_i$ can also be used in a simplified variant. In this case, the information on changing the surface F→F' is no longer transferred in full in the contact pressure transformation AT. Instead, a suitable approximation surface N which is subjected to the transformation AT is selected in the transformed system (contact glass system). Characteristic points $f_i$ are again selected for the approximation surface and converted into transformed points $f_i'$ with the contact pressure transformation AT. An interpolation surface I' which connects (or approximates) the transformed points $f_i'$ is then again found by interpolation (if required by approximation).

The deviation between the actual correction surface F and the approximation surface N is also taken into account. To do so, the deviation D between the surfaces F and N is determined in the untransformed system. This deviation D can be determined in different ways. Firstly, it is possible to determine the deviation D for all characteristic points $f_i$. There is then a set of deviation values corresponding to the set of characteristic points. Alternatively, it is possible to determine a deviation function D.

The deviation D is then used to correct the interpolation surface I'. Either the interpolation surface I' is corrected with it after the interpolation or the transformed characteristic points f' are corrected with the deviation D and the interpolation surface I then determined. The latter is expedient when a set of deviation parameters is fixed for the set of characteristic points. Thus the following features are provided or possible:

1. The information about the cut surface F in the natural system is reduced by determining the approximation surface N. This is carried out by determining the approximation surface N for the cut surface F, for example a sphere or a Zernicke polynomial with a reduced order compared with the cut surface.

2. Characteristic points $f_i$ are determined for N. Advantageously symmetries of the surface N are considered. It is also advantageous to take into account invariances of the angle imaging in the contact pressure transformation (angle about the optical axis) when choosing the points.

3. The deviation D of the cut surface F from the approximation surface N in the natural system (eye system) is determined.

4. The points $f_i$ are transformed into $f_{i'}$ and the interpolation surface I' determined.

5. The symmetry properties of the interpolation surface I' then deviate only slightly from the approximation surface N in the untransformed system.

6. In order to transform the cut surface F as good as possible, the deviation D is applied to I', so that a function results which is a good representative of a transformed version of cut surface F.

7. The deviation D can be applied both to the interpolation surface I' an to the transformed points $f_i'$, as already mentioned.

8. It is advantageous to adapt the interpolation surface to the transformed characteristic points $f_i'$ such that one of the parameters of the function is the height z. Naturally, a substitute in a known relationship thereto can also be used. The same applies to the deviation D.

The use of pulsed laser radiation is not the only way in which surgical refraction correction can be carried out. The determination, described here, of control data for operating the device can be used for almost any operating procedure in which, by means of a device, with control by control data, a volume is removed from the cornea or added to it, as already explained in the general section of the description.

The invention claimed is:

1. A method for generating control data that control a laser for surgical correction of defective vision of an eye of a patient, wherein, prior to application of the laser to a cornea, the cornea is brought from an undeformed state to a deformed state by pressing a front surface of the cornea against a contact surface; the method comprising:
    a) predetermining a correction surface by application of a control unit, which correction surface relates to the cornea in the undeformed state and is to be produced for correction of defective vision as a cut surface in the cornea;
    b) selecting several points lying in the correction surface or in an approximation surface derived therefrom by application of the control unit, the several points being a subset of points lying in the correction surface or the approximation surface derived therefrom;
    c) generating transformed points by transforming by application of the control unit, coordinates of the selected points into coordinates of the same points for the cornea in the deformed state to compensate for the deformed state of the cornea during operation of the laser;
    d) generating an interpolation surface by interpolating between the transformed points by application of the control unit; and
    e) selecting target points lying on the interpolation surface by application of the control unit; and
    f) using the target points for generating the control data.

2. The method according to claim 1, further comprising, before b) deriving the approximation surface from the correction surface by a smoothing or approximation process by application of the control unit, and before step e) determining a deviation between the correction surface and the approximation surface and correcting the interpolation surface using the deviation by application of the control unit.

3. A device, the device including a control unit that generates control data, the control data controlling a laser for surgical correction of defective vision of an eye of a patient, wherein, prior to application of the laser, a cornea of the eye is brought from an undeformed state to a deformed state by pressing a front surface of the cornea against a contact surface and wherein a correction surface is predetermined for the non-deformed cornea, which correction surface relates to the cornea in the undeformed state and is to be produced for correction of defective vision as a cut surface in the cornea, and
    wherein
        A) the control unit, when generating the control data, selects several points lying in the correction surface or in an approximation surface derived therefrom, the several points being a subset of points lying in the correction surface or the approximation surface derived therefrom;
        B) the control unit generates transformed points by transforming coordinates of the selected points into coordinates of the same points for the cornea in the deformed state to compensate for the deformed state of the cornea during operation of the laser,
        C) the control unit, generates an interpolation surface by interpolation between the transformed points; and
        D) the control unit, selects target points lying on the interpolation surface; and
        E) the control unit generates the control data by using the target points.

4. The device according to claim 3, wherein before performing A) the control unit, derives the approximation surface from the correction surface by a smoothing or approximation process, and before D) determines a deviation between the correction surface and the approximation surface and corrects the interpolation surface by using this deviation.

5. A non-transitory computer readable medium that is not a carrier wave or signal and that includes instructions to cause a computer to execute a method for generating control data that control a laser for surgical correction of defective vision of an eye of a patient, wherein prior to application of the laser a cornea of the eye is brought from an undeformed state to a deformed state by pressing a front surface of the cornea against a contact surface, the executed method comprising:
    a) predetermining a correction surface, which correction surface relates to the cornea in the undeformed state and is to be produced for correction of defective vision as a cut surface in the cornea;
    b) selecting several points lying in the correction surface or in an approximation surface derived therefrom, the several points being a subset of points lying in the correction surface or the approximation surface derived therefrom
    c) generating transformed points by transforming coordinates of the selected points into coordinates of the same points for the cornea in the deformed state to compensate for the deformed state of the cornea during operation of the laser;
    d) generating an interpolation surface by interpolation between the transformed points; and
    e) selecting target points lying on the interpolation surface; and
    f) using the target points for generating the control data.

* * * * *